Figure 2:
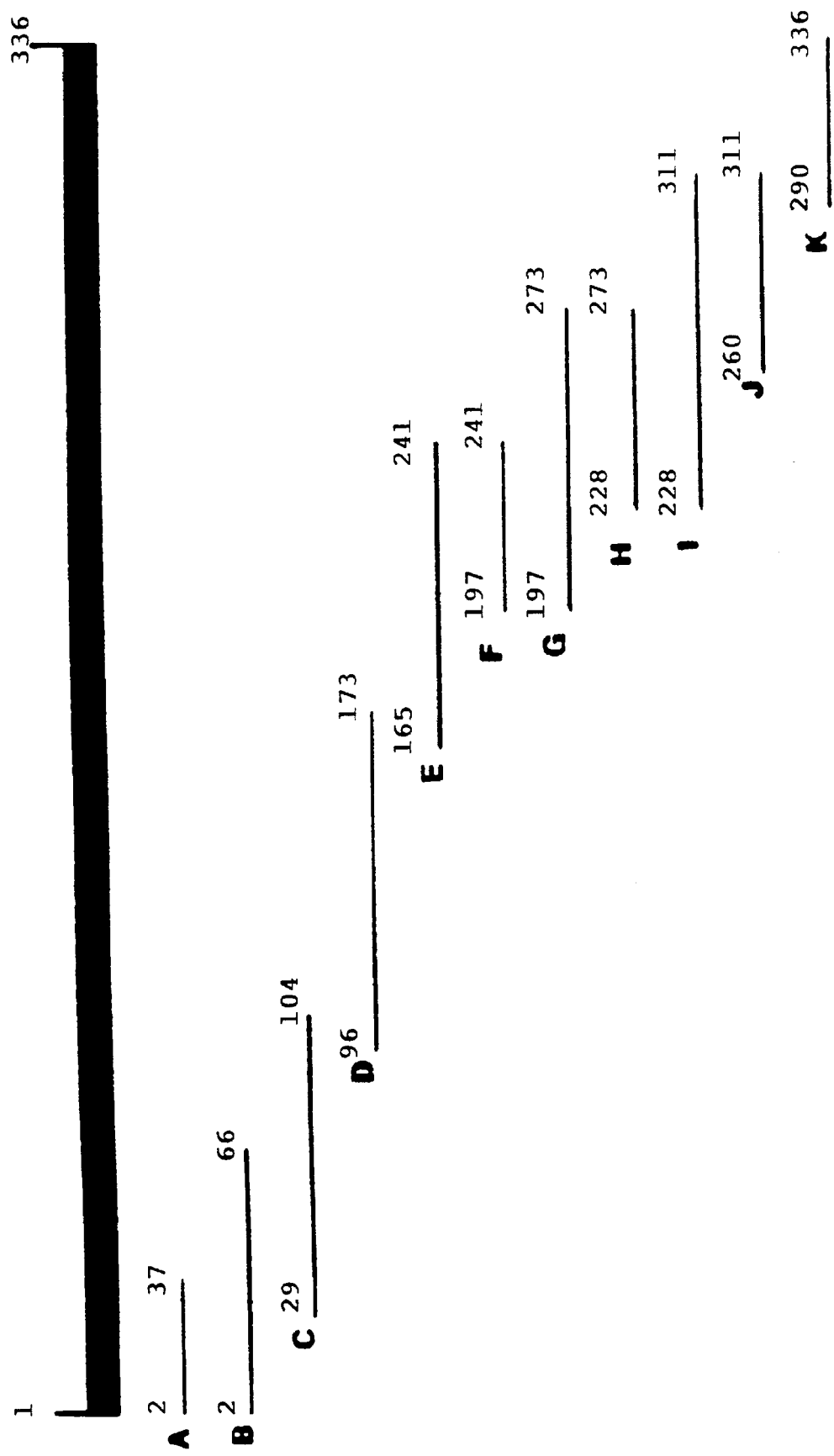

United States Patent [19]

Flavell et al.

[11] Patent Number: 5,618,533
[45] Date of Patent: Apr. 8, 1997

[54] FLAGELLIN-BASED POLYPEPTIDES FOR THE DIAGNOSIS OF LYME DISEASE

[75] Inventors: Richard A. Flavell, Killingworth; Erol Fikrig, Guilford, both of Conn.; Robert Berland, Kingston, N.Y.

[73] Assignee: Yale University, New Haven, Conn.

[21] Appl. No.: 166,160

[22] Filed: Dec. 10, 1993

Related U.S. Application Data

[63] Continuation of Ser. No. 837,193, Feb. 11, 1992, abandoned.
[51] Int. Cl.$^6$ .............. C07K 5/00; C07H 21/04; C12N 15/00; G01N 33/536
[52] U.S. Cl. .............. 424/184.1; 530/350; 530/300; 530/825; 530/387.5; 435/13; 435/197; 435/11; 435/192; 435/132; 435/975; 536/23.4; 436/536; 436/347; 436/548; 436/800
[58] Field of Search .............. 424/88, 184.1; 435/7.3, 7.1 T, 7.92, 7.32, 69.7, 975; 530/350, 825, 300, 389.5; 536/23.4; 436/536, 547, 548, 800

[56] References Cited

U.S. PATENT DOCUMENTS 5,187,065  2/1993  Schutzer .............. 435/7.32

FOREIGN PATENT DOCUMENTS 9004411  5/1990  WIPO.
9109870  7/1991  WIPO.

OTHER PUBLICATIONS

Steere, A.C. (89) New Engl. J. Med. 324: 586–596.
Grodeicki, R.L. et al (88) J. Inf. Dis. 157:790–797.
Coleman, J.L. et al. (87) J. Inf. Dis. 155:756–765.
Wallich, R. et al (90) Inf. Imm. 58:1711–1719.
Gassman, G.S. et al. (91) J. Bacteriol. 173:1452–1459.
Berland, R. et al (91) Inf. Imm. 59:3531–3535.
Rasiah, C. et al. (92) J. Gen. Microbiol. 138–147–154.
E. Aberr et al., "Molecular Mimicry and Lyme Borreliosis: A Shared Antigenic Determinant Between *Borrelia burgdorferi* and Human Tissue", *Ann. Neurol.*, 26, pp. 732–737 (1989).
A.G. Barbour et al., "A *Borrelia*–Specific Monoclonal Antibody Binds to a Flagellar Epitope", *Infec. Immun.*, 52, pp. 549–554.
R. Berland et al., "Molecular Characterization of the Humoral Response to the 41–Kilodalton Flagellar Antigen of *Borrelia burgdorferi*, the Lyme Disease Agent", *Infect. Immun.*, 59, pp. 3531–3535 (1991).
J.L. Coleman and J.L. Benach, "Isolation of Antigenic Components from the Lyme Disease Spirochete: Their Role in Early Diagnosis", *J. Infect. Dis.*, 155, pp. 756–765 (1987).
J.L. Coleman and J.L. Benach, "Identification and Characterization of an Endoflagellar Antigen of *Borrelia burgdorferi*", *J. Clin. Invest.*, 84, pp. 322–330 (1989).
C. Collins nd G. Peltz, "Immunoreactive Epitopes on an Expressed Recombinant Flagellar protein of *Borrelia burgdorferi*", *Infect. Immun.*, 59, pp. 514–520 (1991).

J.E. Craft et al., "Antibody Response in Lyme Diseade: Evaluation of Diagnostic Tests", *J. Infec. Dis.*, 149, pp. 789–795 (1984).
J.E. Craft et al., "Antigens Of *Borrelia burgdorferi* Recognized during Lyme Disease", *J. Clin. Invest.*, 78, pp. 934–939 (1986).
G.S. Gassmann et al., "Analysis of the *Borrelia burgdorferi* GeHo Antigenic Charachterization of Its Gene Product", *J. Bacteriol.*, 173, pp. 1452–1459 (1991).
G.S. Gassmann et al., "Nucleotide sequence of a gene encoding the *borrelia burgdorferi* flagellin", *Nuc. Acids Res.*, 17, p. 3590 (1989).
R.L. Grodzicki and A.C. Steere, "Compariosn of Immunoblotting and Indirect Enzyme–Linked Immunosorbent Assay Using Different Antigen Prepara tions for Diagnosing Early Lyme Disease", *J. Inf. Dis.*, 157, pp. 790–797 (1988).
K. Hansen et al., "Measurement of Antibodies to the *Borrelia burgdorferi* Flagellum Improves Serodiagnosis in Lyme Disease", *J. Clin. Microbiol.*, 26, pp. 338–346 (1988).
M.D. Kramer et al., "Characterization of *Borrelia burgdorferi* Associated Antigens by Monoclonal Antibodies", *Immunobiol.*, 181, pp. 357–366 (1990).
B.J. Luft et al., "Biochemical and Immunological Characterization of the Surface Proteins of *Borrelia burgdorferi*", *Infect. Immun.*, 57, pp. 3637–3645 (1989).
S.W. Luger and E. Krauss, "Serologic Tests for Lyme Disease: Interlaboratory Variability", *Arch. Intern. Med.*, 150, pp. 761–763 (1990).
L.A. Magnarelli et al., "Cross–Reactibity in Serological Tests for Lyme Disease and other Spirochetal Infections", *J. Infect. Dis.*, 156, pp. 183–188 (1987).
L.A. Magnarelli etal., "Cross–Reactivity of Nonspecific Treponemal Antibody in Serologic Tests for Lyme Disease", *J. Clin. Microbiol.*, 28, pp. 1276–1279 (1990).
L. H. Sigal and A.H. Tatum, "Lyme disease patients serum contains igM antibodies to *Borrelia burdorferi* that cross–react with neuronal antigens", *Neurology*, 38, pp. 1439–1442 (1988).
R. Wallich et al., "The *Borrelia burgdorferi* Flagellum–Associated 41–Kilodalton Antigen (Flagellin): Molecular Cloning, Expression and Amplification of the Gene". *Infect. Immun.*, 58, pp. 1711–1719 (1990).
Weiner, H.L. et al. (1991) Ann. Y Acad. Sci. 636–227–232.
Schneider, T. et al. (1991) Inf. Immun. 60:316–319.

(List continued on next page.)

*Primary Examiner*—James C. Housel
*Assistant Examiner*—N. M. Minnifield
*Attorney, Agent, or Firm*—Fish & Neave; James F. Haley, Jr., Esq.; Madge r. Kanter, Esq.

[57] ABSTRACT

Diagnostic means and methods for Lyme disease comprising *B. burgdorferi* flagellin polypeptides and antibodies. Compositions and methods comprising neuroborreliosis-associated antigens useful for the detection, treatment and prevention of neuroborreliosis, arthritis, carditis and other manifestations of Lyme disease.

11 Claims, 7 Drawing Sheets

OTHER PUBLICATIONS

Kumar et al. 1990. Amino Acid Variahons at a single residue in an autoimmune peptide profoundly affect . . . PNAS 87: 1337–41.

Steere 1989. Medical Progress: Lyme Disease New England J. of Medicine 321(9):586–596.

Gassman et al. 1990 "Molecular Analysis of *Borrelia Burdorferi* Flagllin". IV International Conference on Lyme Borrelions Abstract W–L–5 p6.

Houghten et al. 1986. Relative Importance of position and Individual amino acid . . . in Vaccines 86 d. Brown et al. pp. 21–25.

G.S. Gassman et al., "Molecular Analysis of the *Borrelia Burgdorferi* Flagellin," IV International Conference on Lyme Borreliosis, Abstract W–L–5, p. 6, Stockholm, Sweden (1990).

Fragment A:

5' Oligonucleotide

ATAGAATTC$^4$ATTATCAATCATAATACATCA$^{24}$ (SEQ ID NO: 4)

3' Oligonucleotide

ATAGGATCC$^{111}$ATTAATTCTGTACCC$^{97}$ (SEQ ID NO: 5)

Fragment B:

5' Oligonucleotide

ATAGAATTC$^4$ATTATCAATCATAATACATCA$^{24}$ (SEQ ID NO: 4)

3' Oligonucleotide

ATAGGATCC$^{198}$AGTATTTCTAGAAGC$^{184}$ (SEQ ID NO: 6)

Fragment C:

5' Oligonucleotide

ATAGAATTC$^{85}$AAGCTTTCTAGTGGG$^{99}$ (SEQ ID NO: 7)

3' Oligonucleotide

ATAGGATCC$^{312}$ATCTGAATATGTGCC$^{298}$ (SEQ ID NO: 8)

Fragment D:

5' Oligonucleotide

ATAGAATTC$^{286}$CAATCAGGTAACGGC$^{300}$ (SEQ ID NO: 9)

3' Oligonucleotide

ATAGGATCC$^{519}$TAAAGTCCAAGACGC$^{505}$ (SEQ ID NO: 10)

FIGURE 1A

Fragment E:

5' Oligonucleotide

<u>ATAGAATTC</u>$^{493}$TCAGGGTCTCAAGCG$^{507}$ (SEQ ID NO: 11)

3' Oligonucleotide

<u>ATAGGATCC</u>$^{723}$TGTAACATTAACAGG$^{709}$ (SEQ ID NO: 12)

Fragment F:

5' Oligonucleotide

<u>ATAGAATTC</u>$^{589}$CTTTTCTCTGGTGAG$^{603}$ (SEQ ID NO: 13)

3' Oligonucleotide

<u>ATAGGATCC</u>$^{723}$TGTAACATTAACAGG$^{709}$ (SEQ ID NO: 12)

Fragment G:

5' Oligonucleotide

<u>ATAGAATTC</u>$^{589}$CTTTTCTCTGGTGAG$^{603}$ (SEQ ID NO: 13)

3' Oligonucleotide

<u>ATAGGATCC</u>$^{819}$TCTATTTTGGAAAGC$^{805}$ (SEQ ID NO: 14)

Fragment H:

5' Oligonucleotide

<u>ATAGAATTC</u>$^{682}$GCACCTTCTCAAGGC$^{696}$ (SEQ ID NO: 15)

3' Oligonucleotide

<u>ATAGGATCC</u>$^{819}$TCTATTTTGGAAAGC$^{805}$ (SEQ ID NO: 14)

FIGURE 1B

Fragment I:

5' Oligonucleotide

<u>ATAGAATTC</u>$^{682}$GCACCTTCTCAAGGC$^{696}$ (SEQ ID NO: 15)

3' Oligonucleotide

<u>ATAGGATCC</u>$^{933}$ACTATTAGTTGTTGC$^{919}$ (SEQ ID NO: 16)

Fragment J:

5' Oligonucleotide

<u>ATAGAATTC</u>$^{778}$ATAAGTGATCAAAGG$^{792}$ (SEQ ID NO: 17)

3' Oligonucleotide

<u>ATAGGATCC</u>$^{933}$ACTATTAGTTGTTGC$^{919}$ (SEQ ID NO: 16)

Fragment K:

5' Oligonucleotide

<u>ATAGAATTC</u>$^{895}$ACAATGACAGATGAG$^{909}$ (SEQ ID NO: 18)

3' Oligonucleotide

<u>ATAGGATCC</u>$^{1111}$TTATCTAAGCAATGACAAAAC$^{991}$ (SEQ ID NO: 3)

FIGURE 1C

FLAGELLIN EPITOPE

| PATIENT NO. | 1 | 2 | 3 | 4 | 5 | 6 | 7 | 8 | 9 |
|---|---|---|---|---|---|---|---|---|---|
| 1 | ♦ | ♦ | ♦ ♦ | ♦ ♦ | ♦ ♦ | ♦ ♦ | | | ♦ ♦ |
| 2 | | ♦ | ♦ | ♦ | ♦ | | | | ♦ |
| 3 | | | ♦ | ♦ ♦ | ♦ ♦ | ♦ ♦ | | | ♦ ♦ |
| 4 | | | ♦ | ♦ ♦ | ♦ ♦ | ♦ ♦ | | | ♦ ♦ |
| 5 | | | ♦ | ♦ ♦ | ♦ ♦ | ♦ | | | ♦ ♦ |
| 6 | | | | ♦ | ♦ ♦ | ♦ ♦ | ♦ | | ♦ ♦ |
| 7 | ♦ | | | ♦ | ♦ | | | | ♦ |
| 8 | | | ♦ | ♦ | ♦ | | | | ♦ |
| 9 | | | ♦ | ♦ | ♦ | | | | ♦ |
| 10 | | | ♦ ♦ | ♦ ♦ | ♦ ♦ | ♦ | | | ♦ ♦ |
| 11 | | | ♦ ♦ | ♦ ♦ | ♦ ♦ | | | | ♦ ♦ |
| 12 | | | | ♦ | ♦ | ♦ | | | ♦ |
| 13 | | | | ♦ | ♦ | ♦ | | | ♦ |
| 14 | | | | ♦ ♦ | ♦ ♦ | | ♦ | | ♦ ♦ |
| 15 | | ♦ | | ♦ | | | | | ♦ ♦ |
| 16 | | | ♦ ♦ | ♦ | | | | | ♦ |
| 17 | | | ♦ | ♦ | | | | | ♦ |
| 18 | | | ♦ | ♦ | | | | | ♦ |
| 19 | | | | ♦ | ♦ ♦ | | | | ♦ ♦ |
| 20 | | | | ♦ | ♦ | | | | ♦ |
| 21 | | | | | ♦ ♦ | ♦ ♦ | | | ♦ ♦ |
| 22 | | | | | ♦ | ♦ | | | ♦ |
| 23 | | | | | | ♦ | ♦ | | ♦ ♦ |
| 24 | | | ♦ ♦ | | | | | | ♦ ♦ |
| 25 | | | ♦ | | | | | | ♦ |
| 26 | | | | ♦ ♦ | | | | | ♦ ♦ |
| 27 | | | | ♦ | | | | | ♦ |
| 28 | | | | ♦ | | | | | ♦ |
| 29 | | | | | ♦ | | | | ♦ ♦ |
| 30 | | | | | ♦ | | | | ♦ |
| 31 | | | | | | | | | ♦ |
| 32 | | | | | | | | | ♦ |
| 33 | | | | | | | | | ♦ |
| 34 | | | | | | | | | ♦ |
| 35 | | | | | | | | | ♦ |
| 36 | | | | | | | | | |
| 37 | | | | | | | | | |

FIGURE 3

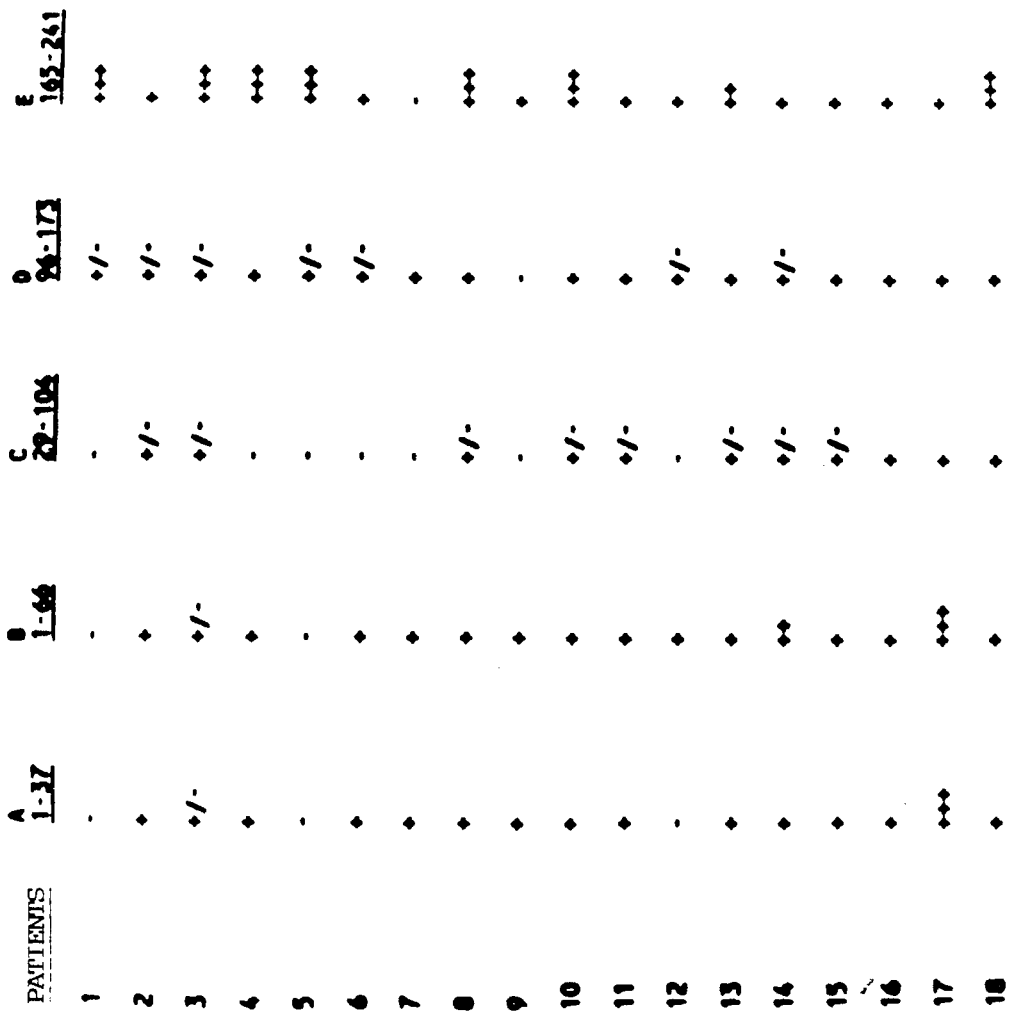

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Glu Gly Val Gln Gln Glu Gly Ala Gln Gln Pro Ala
1               5                   10

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGAGGATCCA TGATTATCAA TCATAATACA    30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGAGAATTCT TATCTAAGGA ATGACAAAAC    30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATAGAATTCA TTATCAATCA TAATACATCA                                         30

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATAGGATCCA TTAATTCTGT ACCC                                               24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ATAGGATCCA GTATTTCTAG AAGC                                               24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ATAGAATTCA AGCTTTCTAG TGGG                                               24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ATAGGATCCA TCTGAATATG TGCC                                               24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATAGAATTCC AATCAGGTAA CGGC                                               24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

ATAGGATCCT AAAGTCCAAG ACGC 24

( 2 ) INFORMATION FOR SEQ ID NO:11:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

ATAGAATTCT CAGGGTCTCA AGCG 24

( 2 ) INFORMATION FOR SEQ ID NO:12:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

ATAGGATCCT GTAACATTAA CAGG 24

( 2 ) INFORMATION FOR SEQ ID NO:13:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

ATAGAATTCC TTTTCTCTGG TGAG 24

( 2 ) INFORMATION FOR SEQ ID NO:14:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

ATAGGATCCT CTATTTGGA AAGC 24

( 2 ) INFORMATION FOR SEQ ID NO:15:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

ATAGAATTCG CACCTTCTCA AGGC 24

( 2 ) INFORMATION FOR SEQ ID NO:16:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

ATAGGATCCA CTATTAGTTG TTGC 24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:17:

ATAGAATTCA TAAGTGATCA AAGG     24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

ATAGAATTCA CAATGACAGA TGAG     24

(2) INFORMATION FOR SEQ ID NO:19:

(i) SEQUENCE CHARACTERISTICS:
        (A) LENGTH: 108 amino acids
        (B) TYPE: amino acid
        (D) TOPOLOGY: linear (ii) MOLECULE TYPE: peptide (xi) SEQUENCE DESCRIPTION: SEQ ID NO:19:

```
Ser Gly Ser Ala Ser Trp Thr Leu Arg Val His Val Gly Ala Asn Arg
 1               5                  10                  15
Asp Glu Ala Ile Ala Val Asn Ile Tyr Ala Ala Asn Val Ala Asn Leu
            20              25                      30
Phe Ser Gly Glu Gly Ala Gln Thr Ala Gln Ala Ala Pro Val Gln Glu
        35              40                      45
Gly Val Gln Gln Glu Gly Ala Gln Gln Pro Ala Pro Ala Thr Ala Pro
    50              55                  60
Ser Gln Gly Gly Val Asn Ser Pro Val Asn Val Thr Thr Thr Val Asp
65              70                  75                      80
Ala Asn Thr Ser Leu Ala Lys Ile Glu Asn Ala Ile Arg Met Ile Ser
            85                      90                  95
Asp Gln Arg Ala Asn Leu Gly Ala Phe Gln Asn Arg
            100             105
```

FLAGELLIN-BASED POLYPEPTIDES FOR THE DIAGNOSIS OF LYME DISEASE

This is a continuation of application Ser. No. 837,193, filed Feb. 11, 1992, entitled FLAGELLIN-BASED COMPOSITIONS AND METHODS FOR THE DIAGNOSIS AND TREATMENT OF LYME DISEASE, now abandoned.

TECHNICAL FIELD OF THE INVENTION

This invention relates to flagellin-based compositions and methods useful for the diagnosis and treatment of Lyme disease. More particularly, this invention relates to flagellin polypeptides which are useful to detect the presence of *B. burgdorferi* in humans and other animals, and which are useful to diagnose and treat neuroborreliosis, arthritis, carditis and other manifestations of Lyme disease. Also within the scope of this invention are antibodies directed against the flagellin polypeptides and diagnostic kits comprising the antibodies or polypeptides.

BACKGROUND OF THE INVENTION

Lyme borreliosis is the most common vector-borne infection in the United States [S. W. Barthold, et al., "An Animal Model For Lyme Arthritis", *Ann. N.Y. Acad. Sci.*, 539, pp. 264–73 (1988)]. It has been reported in every continent except Antarctica. The clinical hallmark of Lyme Disease is an early expanding skin lesion known as erythema migrans (ECM), which may be followed weeks to months later by neurologic, cardiac, and joint abnormalities.

The causative agent of Lyme disease is a spirochete known as *Borrelia burgdorferi*, transmitted primarily by ixodes ticks that are part of the *Ixodes ricinus* complex. *B. burgdorferi* has also been shown to be carried in other species of ticks and in mosquitoes and deer flies, but it appears that only ticks of the *I. ricinus* complex are able to transmit the disease to humans.

Lyme disease generally occurs in three stages. Stage one involves localized skin lesions (ECM) from which the spirochete is cultured more readily than at any other time during infection [B. W. Berger et al., "Isolation And Characterization Of The Lyme Disease Spirochete From The Skin Of Patients With Erythema Chronicum Migrans", *J. Am. Acad. Dermatol.*, 3, pp. 444–49 (1985)]. Flu-like or meningitis-like symptoms are common at this time. Stage two occurs within days or weeks, and involves spread of the spirochete through the patient's blood or lymph to many different sites in the body including the brain and joints. Varied symptoms of this disseminated infection occur in the skin, nervous system, and musculoskeletal system, although they are typically intermittent. Stage three, or late infection, is defined as persistent infection, and can be severely disabling. Chronic arthritis, and syndromes of the central and peripheral nervous system appear during this stage, as a result of the ongoing infection and perhaps a resulting auto-immune disease [R. Martin et al., "*Borrelia burgdorferi*—Specific And Autoreactive T-Cell Lines From Cerebrospinal Fluid In Lyme Radiculomyelitis", *Ann Neurol.*, 24, pp 509–16 (1988)].

The neurologic manifestations of Lyme disease are protean and include weakness, peripheral nerve palsy, radiculitis, meningitis and encephalitis. The pathogenesis of neuroborreliosis, however, is unclear. Examination of the cerebrospinal fluid (CSF) of patients with neuroborreliosis shows a mononuclear pleocytosis and production of *B. burgdorferi* specific antibody, suggesting that inflammation is involved in disease. In some cases, spirochetes have been cultured from the CSF of patients with neurologic symptoms, implicating the organism directly with disease. Experiments using mice suggest that spirochete virulence may play a role in the development of neurologic infection.

Infection with *B. burgdorferi* induces a strong humoral immune response. Early in human infection, antibodies are generated primarily against the 41-kDa flagellar protein. In later stages, antibodies to the outer surface proteins OspA and OspB, among others, appear [J. E. Craft et al., "Antigens Of *Borrelia burgdorferi* Recognized During Lyme Disease", *J. Clin. Invest.*, 78, pp. 934–39 (1986)].

Antibodies to the *B. burgdorferi* flagellin antigen remain prominent in patient serum during infection, and local CSF antibody production to spirochetal antigens, including flagellin, occurs. Further, the sera from patients with neurologic manifestations of Lyme disease have IgM antibodies that bind human axons; binding is weak or absent in patients without neurologic disease. The presence of high antibody titers in the CSF correlates with clinical signs of neuroborreliosis.

At present, all stages of Lyme disease are treated with antibiotics. Treatment of early disease is usually effective, however the cardiac, arthritic and nervous system disorders associated with the later stages often do not respond to therapy [A. C. Steere, "Lyme Disease", *N. Engl. J. Med.*, 321, pp. 586–96 (1989)].

At present, Lyme disease is diagnosed primarily by serology. The enzyme-linked immunosorbent assay (ELISA) is one method of detection, using sonicated whole spirochetes as the antigen [J. E. Craft et al., "The Antibody Response In Lyme Disease: Evaluation Of Diagnostic Tests", *J. Infect. Dis.*, 149, pp. 789–95 (1984)]. However, serologic testing is not yet standardized, and results may vary between laboratories and commercial kits, causing false negative and, more commonly, false positive results [S. Luger and E. Kraus, "Serologic Tests For Lyme Disease: Interlaboratory Variability," *Arch. Int. Med.*, 150, pp. 761–63 (1990)]. In addition, available serologic tests have limited usefulness early in infection prior to the development of a measurable antibody response [R. Grodzickiano and A. C. Steere, "Comparison Of Immunoblotting And Enzyme Linked Immunosorbent Assay Using Different Antigen Preparations For Diagnosing Early Lyme Disease," *J. Inf. Dis.*, 157, pp. 790–97 (1988)].

Because the *B. burgdorferi* flagellar antigen is detectable early in infection, it could potentially prove useful in a diagnostic test. However, the flagellar protein is known to contain epitopes which are conserved among other spirochetes [J. L. Coleman and J. L. Benach, "Identification And Characterization Of An Endoflagellar Antigen Of *Borrelia burgdorferi*", *J. Clin. Invest.*, 84, pp. 322–330 (1989)], and the flagellin cross-reacts with antibodies directed against other bacterial flagellins [L. A. Magnarelli et al., "Cross-Reactivity Of Nonspecific Treponemal Antibody In Serologic Tests For Lyme Disease", *J. Clin. Microbiol.*, 28, pp. 1276–1279 (1990)]. As a result, antibodies to this protein do not provide a specific marker for Lyme disease.

In view of the above, there exists an urgent need for a highly specific and sensitive laboratory test for detection of *B. burgdorferi* infection and diagnosis of Lyme disease. There also exists a need for therapeutic agents and methods of diagnosis and treatment that are useful in later stages of Lyme disease.

DISCLOSURE OF THE INVENTION

The present invention solves the problems referred to above by providing in one preferred embodiment, flagellin polypeptides that comprise an immunodominant region of the *B. burgdorferi* flagellin antigen. The flagellin polypeptides of this invention are recognized by sera from Lyme disease patients but have substantially no homology to other bacterial flagellins and thus do not result in false-positive diagnostic test results.

In another embodiment, this invention provides diagnostic means and methods characterized by flagellin polypeptides and antibodies directed against those polypeptides. These means and methods are useful for the diagnosis of Lyme disease and the detection of *B. burgdorferi* infection. They are also useful in following the course of treatment against such infection.

In another embodiment, this invention provides neuroborreliosis-associated antigens and pharmaceutically effective compositions and methods comprising those antigens, which are useful for the treatment of prevention of the later stages of Lyme disease. The preferred compositions and methods of this embodiment are characterized by antigens that are recognized by antibodies in the serum of patents with neuroborreliosis, which antibodies also bind to antigens associated with neuronal tissue.

BRIEF DESCRIPTION OF THE FIGURES

FIG. 1 depicts the nucleotide sequence of the flagellin-based oligonucleotides used to PCR amplify fragments A–K of the *B. burgdorferi* flagellin gene. The numbers correspond to the numbering system used in G. S. Gassman et al., "Nucleotide Sequence Of A Gene Encoding The *Borrelia burgdorferi* Flagellin", *Nuc. Acid Res.,* 17, p. 3590 (1989).

FIG. 2 depicts the sizes and locations of flagellin fragments A–K on the map of the full-length *B. burgdorferi* flagellin antigen.

FIG. 3 depicts, in tabular form, the results of immunoblot analyses in which flagellin fragments A–K were tested for their reactivity with sera from patients with Lyme disease.

FIG. 4 depicts, in tabular form, the results of immunoblot analyses in which flagellin fragments F1–F9 were tested for their reactivity with sera from patients with Lyme disease.

DETAILED DESCRIPTION OF THE INVENTION

The present invention relates to novel flagellin peptides and polypeptides, antibodies directed against the peptides and polypeptides, compositions containing the peptides, polypeptides or antibodies, and methods for the detection, treatment and prevention of Lyme disease. More specifically, in one embodiment, this invention relates to diagnostic means and methods comprising flagellin polypeptides which are effective to specifically detect *B. burgdorferi* infection in humans and other animals.

In another embodiment, this invention relates to anti-flagellin polypeptide antibodies, and diagnostic means and methods comprising those antibodies, which are effective to detect *B. burgdorferi* infection in humans and other animals.

In another embodiment, this invention relates to compositions and methods comprising neuroborreliosis-associated antigens which are effective to detect and remove antibodies in the serum of Lyme disease patients, which antibodies cross react with antigens associated with neuronal tissue.

In order to further define this invention, the following terms and definitions are herein provided.

As used herein, "immunodominant region" denotes a region of the *B. burgdorferi* flagellin antigen, or derivatives thereof, that is recognized by antibodies elicited by infection with *B. burgdorferi*, but which has substantially less reactivity than the full-length flagellin protein when reacted with antibodies elicited by infection with other bacteria or treponemes.

As used herein, "substantially less reactivity" means, preferably, that when reacted in an ELISA or on an immunoblot with patient sera which contains antibodies elicited by a treponemal or bacterial infection (other than infection with *B. burgdorferi*), the region would be bound at at least a 10-fold lower level than the level of binding which occurs to the entire flagellin antigen. More preferably, the region would be bound at at least a 50-fold lower level than the level of binding which occurs to the entire flagellin antigen. And, most preferably, there would be no detectable binding.

As used herein, "flagellin polypeptide" denotes a polypeptide comprising an immunodominant region of a *B. burgdorferi* flagellin antigen.

As will be apparent from the disclosure which follows, such immunodominant regions may occur throughout the flagellin antigen.

The preferred flagellin polypeptides of this invention for the detection of *B. burgdorferi* infection comprise an immunodominant region consisting essentially of amino acids 165–273 of a *B. burgdorferi* flagellin protein* (SEQ ID NO: 19) or fragments thereof or derivatives thereof that retain the immunological activity of an immunodominant region. More preferably they comprise an immunodominant region consisting essentially of amino acids 197–273 of a *B. burgdorferi* flagellin protein or fragments thereof or derivatives thereof that retain the immunological activity of an immunodominant region. And, more preferably they comprise an immunodominant region consisting essentially of amino acids 197–241 of a *B. burgdorferi* flagellin protein or fragments thereof or derivatives thereof that retain the immunological activity of an immunodominant region.

*The amino acid numbering system for the *B. burgdorferi* flagellin antigen used throughout this application corresponds to the nucleotide numbering system used in G. S. Gassman et al., supra. Thus, amino acid 1 is encoded by the ATG present at nucleotide positions 1–3 of G. S. Gassman et al., supra.

An unexpected advantage of the flagellin polypeptides of this invention is their high sensitivity. They are capable of detecting *B. burgdorferi*-specific antibodies in the vast majority of confirmed seropositive samples tested. Another advantage of the flagellin polypeptides of this invention is their high level of specificity—a minimal number of false positives due to a very low level of cross-reactivity with antibodies directed against treponemes and other bacteria.

As used herein, an "anti-flagellin polypeptide antibody" denotes an immunoglobulin molecule, or portion thereof, that is immunologically reactive with a flagellin polypeptide of the present invention.

An anti-flagellin polypeptide antibody may be an intact immunoglobulin molecule or a portion of an immunoglobulin molecule that contains an intact antigen binding site, including those portions known in the art as F(v), Fab, Fab' and F(ab')2.

As used herein, a "neuroborreliosis-associated antigen" denotes an antigen comprising a peptide fragment of the *B. burgdorferi* flagellin antigen or derivatives thereof, which fragment is immunologically reactive with antibodies generated by infection of a mammalian host with *B. burgdorferi*, which antibodies are immunologically reactive with antigens associated with neuronal tissue.

The neuroborreliosis-associated antigens that are preferred for use in such methods and compositions, by virtue of the ability to bind to anti-*B. burgdorferi* antibodies and other molecules which may participate in neuroborreliosis, arthritis, carditis and other manifestations of Lyme disease, are useful not only to diagnose and detect these manifestations but are also useful for the prevention and treatment of the aforementioned conditions.

The most preferred neuroborreliosis-associated antigens of this invention comprise the peptide of SEQ ID NO:1 and derivatives thereof or fragments thereof that retain the desired immunological reactivity. In accordance with this invention, we describe a method of treating a patient suffering from neuroborreliosis, arthritis, carditis, or other manifestations of Lyme disease, in a pharmaceutically acceptable manner with a therapeutically effective amount of a neuroborreliosis-associated antigen.

As used herein, a "therapeutically effective amount of a neuroborreliosis-associated antigen" is the amount required to prevent or lessen the severity, for some period of time, of the neuroborreliosis, arthritis, carditis or other manifestations of Lyme disease associated with infection with *B. burgdorferi*.

As will be readily apparent to one of skill in the art, a neuroborreliosis-associated antigen may also be a flagellin polypeptide of this invention.

One of skill in the art will understand that derivatives of the flagellin polypeptides of this invention and the neuroborreliosis-associated antigens of this invention may contain amino acid insertions, deletions, substitutions and modifications at one or more sites in the immunodominant region or the peptide fragment and retain the desired immunological reactivity of the polypeptide and antigens of this invention. Such insertions, substitutions and modifications include, for example, natural amino acids, those amino acids in their D-configuration, and the known non-native, synthetic, and modified amino acids such as homocysteine, ornithine, norleucine and β-valine. Preferred modifications and substitutions to the native amino acid sequence are conservative ones (i.e., those having minimal influence on the secondary structure and hydropathic nature of the peptide). These include substitutions such as those described by Dayhoff in the Atlas of Protein Sequence and Structure 5, 1978 and by Argos in *EMBO J.*, 8, pp. 779–85 (1989).

It should also be understood that a flagellin polypeptide or neuroborreliosis-associated antigen of this invention may be part of a larger protein. For example, it may be fused to a substituent effective to facilitate purification or to improve the immunogenic reactivity. Substituents effective to improve the immunogenic reactivity of the polypeptide or peptide may be flagellin polypeptides or neuroborreliosis-associated antigens themselves, such that the fusion polypeptide contains repeated sequences of the same block of amino acids.

Similarly, the flagellin polypeptide or neuroborreliosis-associated antigen of this invention may also be part of a larger multimeric protein comprising multiple copies of flagellin polypeptides or neuroborreliosis-associated antigens. Such fusion proteins and multimeric proteins may be produced recombinantly, or may be synthesized chemically. They may also include flagellin polypeptides and neuroborreliosis-associated antigens that are fused or coupled to moieties other than amino acids, including lipids and carbohydrates.

One of skill in the art will also understand that it is often useful and certainly within the scope of this invention to modify the flagellin polypeptides and neuroborreliosis-associated antigens of this invention in order to make the chosen polypeptide or peptide more useful as an immunodiagnostic, prophylactic or therapeutic agent. Such changes, for example, include:

addition of a cysteine residue to one or both terminals in order to facilitate coupling to a suitable carrier with heterobifunctional cross-linking reagents;

addition of additional amino acids at one or both terminals of the polypeptide or antigen to facilitate linking to each other, for coupling to a support or larger peptide or protein or for modifying the physical or chemical properties of the polypeptide or antigen;

derivatization of one or both terminals of the polypeptide or antigen by, for example, acylation or amidation. These modifications result in changes in the net charge on the polypeptide or antigen and can also facilitate covalent linking to a solid support, a carrier or another peptide.

The flagellin polypeptides of this invention provide a high degree of diagnostic sensitivity, while keeping diagnostic specificity at a high level as well. One of skill in the art will understand that while larger flagellin polypeptides may be more sensitive, additional flagellin sequences may result in a decrease in specificity. Using the teachings of this invention, however, one of skill in the art can easily make modifications or derivatives of the immunodominant regions within the flagellin polypeptides with the aim of increasing both sensitivity and specificity. For example, any domains in a highly sensitive immunodominant region which are found to have low levels of cross-reactivity with antibodies directed against bacteria and other treponemes could be masked or blocked by constructing a flagellin polypeptide containing modifications or derivatives of the immunodominant region in accordance with the teachings of this invention. In this way the specificity of the flagellin polypeptide may be increased without any concomitant decrease in sensitivity.

One of skill in the art will also understand that the effectiveness of the flagellin polypeptides of this invention as diagnostic agents may be enhanced by combining them with other *B. burgdorferi* antigens, such as OspA or OspB or fragments thereof. Antibodies directed against OspA and OspB will not cross react with the antigens of bacteria and other treponemes, while at the same time, antibodies directed against the flagellin polypeptide are detectable at earlier stages of the disease than OspA and OspB.

It will be readily appreciated by one of ordinary skill in the art that the flagellin polypeptides and neuroborreliosis-associated antigens of this invention may be prepared by recombinant means, chemical means, or combinations thereof.

For example, flagellin polypeptides may be generated by recombinant means using DNA encoding the immunodominant region located between amino acids 197 and 241 of the *B. burgdorferi* strain N40 flagellin antigen, or derivatives of that DNA sequence. Flagellin genes of other *B. burgdorferi* serotypes or derivatives thereof may likewise be cloned and expressed to produce other flagellin polypeptides, e.g., using PCR and oligonucleotide primers derived from the sequence encoding the flagellin polypeptide comprising amino acids 197–241 of the *B. burgdorferi* strain N40 flagellin antigen. Similarly, the neuroborreliosis-associated antigens of this invention may also be generated by recombinant means, for example, using DNA encoding SEQ ID NO:1 or fragments thereof or derivatives thereof.

If the flagellin polypeptides or the neuroborreliosis-associated antigens of this invention are produced recombinantly they may be expressed in unicellular hosts. As is well known to one of skill in the art, in order to obtain high expression levels of foreign DNA sequences in a host, the sequences must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an expression marker useful in the expression host.

The DNA sequences encoding the flagellin polypeptides and neuroborreliosis-associated antigens of this invention may or may not encode a signal sequence. If the expression host is eukaryotic, it generally is preferred that a signal sequence be encoded so that the protein is secreted and matured from the eukaryotic host.

An amino terminal methionine may or may not be present on the expressed flagellin polypeptides and neuroborreliosis-associated antigens of this invention. If the terminal methionine is not cleaved by the expression host, it may, if desired, be chemically removed by standard techniques.

A wide variety of expression host/vector combinations may be employed in expressing the DNA sequences encoding the polypeptides and peptides of this invention. Useful expression vectors for eukaryotic hosts, include, for example, vectors comprising expression control sequences from SV40, bovine papilloma virus, adenovirus, cytomegalovirus and retroviruses. Useful expression vectors for bacterial hosts include known bacterial plasmids, such as plasmids from *E. coli*, including col E1, pCR1, pBR322, pMB9 and their derivatives, wider host range plasmids, such as RP4, phage DNAs, e.g., the numerous derivatives of phage lambda, e.g., NM989, and other DNA phages. Useful expression vectors for yeast cells include the 2μ plasmid and derivatives thereof. Useful vectors for insect cells include pVL 941.

In addition, any of a wide variety of expression control sequences—sequences that control the expression of the DNA sequence when operatively linked to it—may be used in these vectors to express DNA sequences encoding the polypeptides and antigens of this invention. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

In a preferred embodiment, DNA encoding the flagellin polypeptides and neuroborreliosis-associated antigens of this invention is inserted in frame into an expression vector that allows high level expression of the polypeptide or antigen as a fusion protein. Such a fusion protein thus contains amino acids encoded by the vector sequences as well as amino acids of the flagellin polypeptide or antigen. Expression of the polypeptides and antigens as fusion proteins may increase stability and/or facilitate purification.

A wide variety of unicellular host cells are useful in expressing the flagellin polypeptides and neuroborreliosis-associated antigens of this invention. These hosts may include well known eukaryotic and prokaryotic hosts, such as strains of *E. coli*, Pseudomonas, Bacillus, Streptomyces, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells, as well as plant cells in tissue culture. We prefer *E. coli* JM 109, DH5α or A89.

It should of course be understood that not all vectors and expression control sequences encoding the polypeptides and antigens will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with a DNA sequence encoding a polypeptide or peptide of this invention, particularly as regards potential secondary structures. Unicellular hosts should be selected by consideration of their compatibility with the chosen vector, the toxicity of the product their secretion characteristics, their ability to fold the polypeptide or peptide correctly, their fermentation or culture requirements, and the ease of purification from them of the polypeptides and peptides of this invention.

Within these parameters, one of skill in the art may select various vector/expression control sequence/host combinations that will express the DNA sequences of this invention on fermentation or in large scale animal culture, e.g., CHO cells or COS 7 cells.

The molecules comprising the flagellin polypeptides and neuroborreliosis-associated antigens of this invention may be isolated from the fermentation or cell culture and purified using any of a variety of conventional methods including: liquid chromatography such as normal or reversed phase using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

In addition, the flagellin polypeptides and particularly the neuroborreliosis-associated antigens of this invention may be generated by any of several chemical techniques. For example, they may be prepared using the solid-phase synthetic technique originally described by R. B. Merrifield, "Solid Phase Peptide Synthesis. I. The Synthesis of A Tetrapeptide", *J. Am. Chem. Soc.*, 83, pp. 2149–54 (1963), or they may be prepared by synthesis in solution. A summary of peptide synthesis techniques may be found in M. Bodanszky, Principles Of Peptide Synthesis, Springer-Verlag (1984).

Typically, these synthetic methods comprise the sequential addition of one or more amino acid residues to a growing peptide chain. Often peptide coupling agents are used to facilitate this reaction. Normally, either the amino or carboxyl group of the first amino acid residue is protected by a suitable, selectively removable protecting group. A different protecting group is utilized for amino acids containing a reactive side group e.g., lysine. A variety of protecting groups known in the field of peptide synthesis and recognized by conventional abbreviations therein, may be found in T. Greene, *Protective Groups In Organic Synthesis*, Academic Press (1981).

As diagnostic reagents, the flagellin polypeptides of this invention may be used in accordance with any of the diagnostic methods known in the art. These include, for example, ELISA, hemagglutination, single-dot and multi-dot methods and assays.

A preferred convenient and classical technique for the determination of antibodies against *B. burgdorferi* using a flagellin polypeptide of this invention is an enzyme-linked immunosorbent assay (ELISA). In this assay, for example, a flagellin polypeptide of this invention is adsorbed onto, or covalently coupled to, the wells of a microtiter plate. The wells are then treated with the sera or analyte to be tested. After washing, antihuman IgG or anti-human IgM labeled with peroxidase is added to the wells. The determination of the peroxidase is performed with a corresponding substrate, e.g., 3,3'5,5'-tetramethylbenzidine. Without departing from the usefulness of this illustrative assay, the peroxidase can be exchanged by another label, e.g., by a radioactive, fluorescent, chemiluminescent or infra-red emitting label.

Another method for the detection of antibodies against the flagellin polypeptides of this invention is an enzyme immunological test according to the so-called "Double-Antigen-Sandwich-Assay." This method is based on the work of Maiolini, as described in Immunological Methods, 20, 25–34, 1978. According to this method, the serum or other analyte to be tested is contacted with a solid phase on which a flagellin polypeptide of this invention has been coated (capture layer) and with a flagellin polypeptide of this invention which has been labeled with peroxidase or another label (probe layer).

The flagellin polypeptides of this invention are not only useful in the determination and quantification of antibodies against *B. burgdorferi*. They are also useful for the determination and quantification of *B. burgdorferi* antigens themselves, because the flagellin polypeptides of this invention, either free, polymerized or conjugated to an appropriate carrier, are useful in eliciting antibodies, in particular and preferably, monoclonal antibodies, immunologically cross-reactive to the antigens of *B. burgdorferi*.

Such antibodies, for example, can be produced by injecting a mammalian or avian animal with a sufficient amount of the flagellin polypeptide to elicit the desired immune response and recovering said antibodies from the serum of said animals. Suitable host animals for eliciting antibodies include, for example, rabbits, horses, goats, guinea pigs, rats, mice cows, sheep and hens. Preferably, hybridomas producing the desired monoclonal antibodies are prepared using the flagellin polypeptides of this invention and conventional techniques. For a review of such methods, see *Antibodies, A Laboratory Manual*, Cold Spring Harbor laboratory, ed. E. Harlow and D. Lane (1988) and D. E. Yelton et al., *Ann. Rev. Biochem.*, 50, pp. 657–80 (1981).

Various methods which are generally known can be employed in the determination or quantification of *B. burgdorferi* or a portion thereof using the anti-flagellin polypeptide antibodies of this invention. In one such procedure, known amounts of a serum sample or other analyte to be assayed, a radiolabeled flagellin polypeptide of this invention and an unlabeled flagellin polypeptide of this invention are mixed together, a given amount of an anti-flagellin polypeptide antibody, preferably a monoclonal antibody, is added and the mixture allowed to stand. The resulting antibody/antigen complex is then separated from the unbound reagents by procedures known in the art, i.e., by treatment with ammonium sulphate, polyethylene glycol, a second antibody either in excess or bound to an insoluble support, or dextran-coated charcoal. The concentration of the labeled flagellin polypeptide is then determined in either the bound or unbound phase and the *B. burgdorferi* antigen content of the sample determined by comparing the level of labeled component to a standard curve in a manner known per se.

Another suitable assay using the antibodies of this invention to detect or quantify *B. burgdorferi* is the "Double-Antibody-Sandwich-Assay." According to this assay, the sample to be tested is treated with two different antibodies, e.g., raised by immunizing different animals, e.g., sheep and rabbits, with a flagellin polypeptide of this invention. One of the antibodies is labeled and the other is coated on a solid phase. The preferred solid phase is a plastic bead and the preferred label is horse-radish peroxidase.

Typically in the "Double-Antibody-Sandwich-Assay," the sample is incubated with the solid phase antibody and the labeled antibody. After the immunological reaction(s), the mixture is washed and the label is determined according to procedures known in the art. In the case where peroxidase is used as the label, the determination may be performed using a substrate, e.g., with o-phenylene diamine or with tetramethylbenzidine. The amount of the labeled component is proportional to the amount of the antigen present in the analyte or serum sample.

As diagnostic agents, the flagellin polypeptides and anti-flagellin polypeptide antibodies of this invention may be included in a kit which may also comprise instructions for use and other appropriate reagents. The polypeptide or antibody may be labeled with a detection means that allows for the detection of the flagellin polypeptide when it is bound to an antibody, or for the detection of the anti-flagellin polypeptide antibody when it is bound to *B. burgdorferi.*

The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}I$ or $^{51}Cr$ that produces gamma ray emissions, or a radioactive element that emits positrons which produce gamma rays upon encounters with electrons present in the test solution such as $^{11}C$, $^{15}O$, or $^{13}N$.

The linking of the detection means is well known in the art. For instance, monoclonal anti-flagellin antibody molecules produced by a hybridoma can be metabolically labeled by incorporation of radioisotope-containing amino acids in the culture medium, or polypeptides may be conjugated or coupled to a detection means through activated functional groups.

The diagnostic kits of the present invention may be used to detect the presence of a quantity of *B. burgdorferi* or anti-*B. burgdorferi* antibodies in a body fluid sample such as serum, plasma or urine. Thus, in preferred embodiments, a flagellin polypeptide or anti-flagellin polypeptide antibody composition of the present invention is bound to a solid support typically by adsorption from an aqueous medium. Useful solid matrices are well known in the art, and include crosslinked dextran; agarose; polystyrene; polyvinylchloride; cross-linked polyacrylamide; nitrocellulose or nylon-based materials; tubes, plates or the wells of microtiter plates. The polypeptides or antibodies of the present invention may be used as diagnostic agents in solution form or as a substantially dry powder, e.g., in lyophilized form.

Flagellin polypeptides and anti-flagellin polypeptide antibodies provide much more specific reagents than those currently available for diagnosis, and thus may alleviate such pitfalls as false positive and false negative results. One skilled in the art will realize that it may be advantageous in the preparation of such reagents to utilize flagellin polypeptides comprising epitopes from other *B. burgdorferi* proteins, including the OspA and OspB proteins, or non-*B. burgdorferi* proteins, and antibodies directed against such polypeptides.

In order that this invention may be better understood, the following examples are set forth. These examples are for purposes of illustration only, and are not to be construed as limiting the scope of the invention in any manner.

EXAMPLE I—CLONING OF FLAGELLIN POLYPEPTIDES

In order to isolate flagellin polypeptides useful in the compositions and methods of this invention, we began by cloning the entire 41kDa flagellin antigen from *B. burgdorferi* strain N40 [S. W. Barthold et al., "Lyme Borreliosis In Selected Strains And Ages Of Laboratory Mice", *J. Infect. Dis.*, 162 pp 133–38 (1990)], using the polymerase chain reaction (PCR) and synthetic oligonucleotide primers. Spirochetes were grown in 10 ml BSKII medium at 34° C. for 7 days, then harvested by centrifugation at 16 K for 30 minutes. Genomic DNA was purified by SDS lysis and phenol-chloroform extraction as described in F. Hyde and R. Johnson, "Genetic Relationship Of The Lyme Disease Spirochetes To Borrelia, Treponema, and Leptospira", spp *J. Clin. Micro.*, 20, pp 151–54 (1984).

The oligonucleotide primers were derived from the sequence of the 41kDa antigen of *B. burgdorferi* strain B31 [G. S. Gassman et al., "Nucleotide Sequence Of A Gene Encoding The *Borrelia burgdorferi* Flagellin", *Nuc. Acid. Res.*, 16, pp. 3590 (1989)]. The first member of the pair corresponded to the first 21 nucleotides of the coding sequence of the B31 flagellin antigen and included a BamH1 site at the 5' end to facilitate cloning. The second member of the pair corresponded to the complement of the last 20 nucleotides of the flagellin antigen and included an EcoR1 site at the 5' end to facilitate cloning. The sequence of the primers from 5' to 3' (with the restriction sites underlined) was as follows:

(SEQ ID NO: 2) AGAGGATCC$^1$A TGATTATCAA TCAT-AATACA$^{21}$ (SEQ ID NO: 3) AGAGAATTC$^{1111}$T TATCTAAGGA ATGACAAAAC$^{991}$.

We used ten ng of *B. burgdorferi* N40 DNA as a template for a 50 μl PCR reaction performed with Amplitaq polymerase (Perkin Elmer) according to the manufacturer's instructions. We performed thirty cycles consisting of a 1 minute, 94° C. denaturation step, a 1 minute, 40° C. annealing step, and a 3 minute, 72° C. extension step. We then isolated the PCR product by agarose gel electrophoresis and purified it by electroelution onto a DEAE membrane. After digesting the purified DNA with BamH1 and EcoR1, we cloned it into BamH1 and EcoR1 digested pGEX-2T (Pharmacia).

We designated the resulting construct pGEX-2T-41-N40. It encodes a fusion protein containing the glutathione S-transferase gene at its N-terminus and the complete 41kDa flagellin antigen from *B. burgdorferi* strain N40 at its C-terminus. Expression of the fusion protein is under the control of the IPTG-inducible tac promoter and the gene product contains stop codons in all three reading frames at the 3' end.

We next cloned a series of overlapping fragments of the 41kDa flagellin antigen gene by PCR amplification using 10 ng of pMX41-N40 as a template and the pairs of synthetic oligonucleotide primers shown in FIG. 1.

We conducted the reactions as in Example I except that we performed only 25 cycles of amplification, the annealing temperature was in some cases 50° C., and the elongation step was only 2 minutes.

We purified the PCR products using gene clean (BIO 101) according to the manufacturer's instructions or low melting temperature agarose (FMC) using standard procedures [J. Sambrook et al., *Molecular Cloning*, Cold Spring Harbor Laboratory Press, Cold Spring Harbor.] We then digested the purified fragments with EcoR1 and BamH1, subcloned each into similarly digested pMX, and transformed *E. coli* DH5α. The pMX vector (Pharmacia) is a bacterial expression vector identical to pGEX-2T except that the polycloning region of pGEX-2T is replaced with a polycloning region containing, in the 5' to 3' direction, EcoR1, Sma1, BamH1, Sst1, Xho1, and HindIII restriction sites.

We then sequenced cloned fragments B, C, D, E, H, I, and K (which together span the entire flagellin gene) in their entirety by the dideoxy chain termination method. The deduced amino acid sequences of fragments C, H, I, and K were in accord with the published sequences of *B. burgdorferi* strains B31, GeHo [G. S. Gassman et al., "Nucleotide Sequence Of A Gene Encoding The *Borrelia burgdorferi* Flagellin", *Nuc. Acid. Res.*, 16, pp. 3590 (1989)] or CA12 [C. Collins and G. Peltz, "Immunoreactive Epitopes On An Expressed Recombinant Flagellar Protein Of *Borrelia burgdorferi*", *Infect. Immun.*, 59, pp. 514–20 (1991)].

In fragment E, we found an arginine at position 181 (where position 1 is the first amino acid of the intact flagellin) instead of the glutamine found in the strains B31, GeHO and CA12. This presumably reflects a strain difference; the subcloned product of an independent PCR reaction using N40 DNA as a template yielded the same sequence. We also found glycines in fragment D, at positions 105 and 120, which we believe to be the result of PCR artifacts; the products of independent PCR reactions had an alanine at position 105 and a glutamate at position 120.

The sizes and locations of the flagellin fragments which resulted from the cloning are shown in FIG. 2.

A comparison of the derived amino acid sequence of the *B. burgdorferi* flagellin to that of other bacterial flagellins listed in the Genbank database indicates that the N-terminal and C-terminal regions have substantial sequence homology to the N-terminal and C-terminal regions of the flagellins of *Escherichia coli* [G. Kuwajima et al., "Nucleotide Sequence Of The hag Gene Encoding Flagellin Of *Escherichia coli*", *J. Bact.*, 168, pp 1479–83 (1986)], *Salmonella typhimurium* [T. M. Joys, "The Covalent Structure Of The Phase-1 Flagellar Filament Protein Of *Salmonella typhimurium* And Its Comparison With Other Flagellins", *J. Biol. Chem.*, 260, pp 15758–61 (1985)], *Salmonella rubislaw* [L.-N. Wei and T. M Joys, "The Nucleotide Sequence of The H-1' Gene of *Salmonella rubislaw*", *Nuc. Acid. Res.*, 14, pp 8227 (1986)], *Serratia marcescens* [R. M. Harshey et al., "Cloning And Nucleotide Sequence of A Flagellin-Coding Gene (hag) From *Serratia marcescens*", *Gene* 79 pp 1–8 (1989)] and *Roseburia cecicola* [J. H. Martin and D. C. Savage, "Cloning, Nucleotide Sequence, And Taxonomic Implications Of The Flagellin Gene Of *Roseburia cecicola*", *J. Bact.*, 170, pp 2612–17 (1988)]. Such sequence homology easily accounts for the high degree of cross-reactivity between antibodies generated against *B. burgdorferi* and the antigens of other bacteria and treponemes.

EXAMPLE II—EXPRESSION OF FLAGELLIN POLYPEPTIDES

We grew the transformed *E. coli* to an A600 of about 0.5 and induced the bacteria to express high levels of glutathione S-transferase fusion proteins by adding IPTG to a final concentration of 1 mM. We grew the cells in the presence of IPTG for 5 hours at room temperature, then harvested them, resuspended in 1/50 volume of PBS, 1% Triton-X 100 and 1 mM PMSF, and lysed the cells by sonication. We then centrifuged the lysate for 10 minutes in a microfuge to pellet the cellular debris. All the fusion proteins were present in the supernatant except for that containing the full length 41kDa flagellin antigen. We solubilized the pellet containing this protein in 2% SDS but did not purify it further. We loaded the supernatant of the remaining, soluble flagellin fusion proteins onto a glutathione sepharose 4B column (Pharmacia) and eluted with glutathione, according to the manufacturer's instructions.

EXAMPLE III—IDENTIFICATION OF FLAGELLIN POLYPEPTIDES BY IMMUNOBLOT ANALYSIS AND ELISA

We boiled the recombinant fusion proteins from Example II for 5 minutes in sample buffer containing 2% SDS, 100 mM DTT, 50 mM Tris-HCl (pH7.0), ran them on 12.5% SDS polyacrylamide gels, and electroblotted the polypeptides onto nitrocellulose using a Hoeffer Transphor apparatus. We then stained the filters with Ponceau S in 10% TCA, destained in water, blocked for 1 hour with 5% nonfat dry milk in PBS and 0.02% sodium azide, and allowed them to react for 2 hours with various Lyme disease patient sera, diluted 1:300 in blocking solution, which had been preabsorbed overnight with affinity purified glutathione S-transferase linked to cyanogen bromide activated Sepharose 4B.

After incubation with sera, we washed the filters and detected residual bound antibody with $^{125}$I-labeled goat anti-human Ig antibody. We detected bound secondary antibody by autoradiography. The results of the immunoblot analysis are summarized in FIG. 3.

The sera we used for these studies were obtained from Lyme disease patients, most of whom were seen at the Lyme disease clinic of the Department of Rheumatology, Yale University School of Medicine. All patients tested serologically positive on a standard ELISA test using whole sonicated *B. burgdorferi* as antigen. In FIG. 3, patients 5, 8, 16 and 17 had ECM. Patients 2, 4–8, and 10–11 had chronic arthritis of greater than 6 months duration, patient 14 had peripheral neuritis, patient 16 had Bell's Palsey, patient 17 had severe headache and patient 18 had encephalopathy. Patients 1, 3, 9, 12–13 and 15 had arthritis.

As can be seen from FIG. 3, a homogeneous response was observed for most patient sera. Overlapping fragments A and B and fragment D define regions of generally low reactivity. In contrast, seventeen of 18 patient's sera react strongly to the overlapping fragments E, F, and G. Fragments F and G are bound to approximately the same extent in all patients, and fragment H is much more weakly bound.

Sera from two healthy individuals (which also tested negative for *B. burgdorferi* infection in an ELISA) failed to react with any of the fragments. Moreover, we screened 10 additional control sera for 41 kDA and fragment E reactivity and all were negative (data not shown.).

Fragments E, F, and G define a region (amino acids 197–241) that is highly reactive with anti-*B. burgdorferi* antibodies in patient sera, but which does not share significant sequence homology to the flagellins of *Escherichia coli, Salmonella typhimurium, Salmonella rubislaw, Roseburia cecicola* or *Serratia marcescens* (except for four of seven identical amino acids within a short stretch defined by amino acids 209 to 215). Similarly, this region contains only a short segment of homology (four of 6 amino acids identical between amino acids 211–216) with the flagellin protein sequence of *Treponema pallidum* [C. I. Champion et al., "Cloning, Sequencing, And Expression Of Two Class B Endoflagellar Genes Of *Treponema pallidum* subsp. *pallidum* Encoding The 34.5 And 31.0-Kilodalton Proteins", *Infect. Immun.*, 58, pp. 1697–1704 (1990)]. Accordingly, fragments E, F and G should not show substantial reactivity with antibodies directed against other bacteria or treponemes, and thus should represent immunodominant regions that are useful in the flagellin polypeptides of this invention.

To confirm these findings, we performed an immunoblot of fragments A–K using sera from 11 patients with *Treponema pallidum*, the agent of syphilis. The serum samples were obtained from the Connecticut State Laboratory. All the sera had VDRL titers ranging from 1:4 to 1:128 and all were positive by specific fluorescent antibody assay (FTA). We chose syphilitic sera because *B. burgdorferi* is closely related to *Treponema pallidum* and syphilis is the most common spirochetal infection of humans in the United States.

While 10 of the 11 sera bound fragment 41-B, which contains 65 NH$_2$-terminal amino acids of flagellin and thus represents a conservative figure for the level of binding one would expect to see for the full-length flagellin antigen, only two of the sera demonstrated detectable binding to fragment 41G, and that binding was very weak. After prolonged exposure, weak binding to the other fragments was detected.

We also tested the diagnostic effectiveness of the flagellin polypeptides of this invention by ELISA. We coated microtitration plates with 200 microliters per well of recombinant 41-G fusion protein (1 microgram/ml) suspended in 0.05M sodium carbonate, pH 9.6. We also used whole, sonicated *B. burgdorferi* strain 297 as a coating antigen as previously described [J. R. Craft et al., "Antibody Response In Lyme Disease: Evaluation Of Diagnostic Tests", *J. Inf. Dis.*, 149, pp. 789–95 (1984)]. We incubated the plates at 4° C. overnight, then washed with PBS containing 0.05% Tween-20 (PBST). The patient sera we used were diluted 1:100 in PBST and applied in triplicate to each antigen-coated plate at 200 micrograms per well. Plates were then incubated at room temperature for 75 minutes. We then washed the plates three times with PBST. For detection of bound antibody, goat anti-human mu chain alkaline phosphatase conjugate (Sigma) was diluted 1:1000 in PBST and applied at 200 microliters per well to the appropriate plates. We then incubated the plates at room temperature for 45 minutes. After three washes in PBST, p-nitrophenyl phosphate was added to each well. The production of p-nitrophenyl was monitored at 405 nm and the reaction stopped with 3M NaOH when the appropriate positive control wells reached an optical density (A405 value) of 1.0 to 1.5. We calculated the numerical values of the antibody response of patients' sera to each antigen by comparison to standard curves established on each antigen using known positive Lyme disease sera as previously described (J. R. Craft et al. supra).

Briefly, we established standard curves, using serial 2-fold dilutions of known IgM and IgG positive Lyme disease sera, for each antigen, with patients' sera applied to the same plates. In addition, eight known normal sera were run on the same plate, each at a 1:100 dilution; the mean A405 value of these eight sera was set as the cut-off A405 value. The first serial dilution of the standard positive sample that exceeded this cut-off value was assigned a value of 100 antibody units, and a curve relating A405 value to antibody units was established on this basis. The average A405 value for each patient serum was then compared to the standard curve and a value of antibody units was assigned to each serum on the basis of this comparison. A negative titer was <100 units, and titers of 200 to 400 represent reactivity compared to control, positive serum at subsequent 2-fold dilutions. We tested some of the serum samples a minimum of 2 times on separate occasions and in each instance there was never more than a 2-fold difference in the measured antibody levels.

Of the eleven syphilitic serum samples, three (having VDRL titers of 1:8, 1:32 and 1:128) showed weak reactivity with B. burgdorferi, yet none showed reactivity with the 41-G fragment.

Thus, a flagellin polypeptide comprising an immunodominant region corresponding to fragment 41G is highly specific and highly sensitive as well.

In other ELISAs to detect the presence of anti-B. burgdorferi antibodies, we found a high correlation in test results using whole spirochete extract or 41-G as the substrate. However, in a small number of patients, some discrepancies in results yielded by various substrates were noted. Over half of the "discrepant" results occurred with values just above the positive cut-off. Accordingly, as with any diagnostic assay, the sensitivity of diagnostic assays utilizing the flagellin polypeptides of this invention should be rigorously standardized.

As can be seen from FIG. 3, some patients contain antibodies reactive with additional regions of the molecule. These regions may also provide flagellin polypeptides useful in the methods and compositions of this invention.

EXAMPLE IV—IDENTIFICATION OF NEUROBORRELIOSIS-ASSOCIATED ANTIGENS

It is known that antibodies in sera of patients with neurologic manifestations of Lyme borreliosis bind to human neuronal tissue. To identify the antibody binding site common to the B. burgdorferi flagellin protein and human neuronal tissue, we made recombinant fusion proteins expressing specific epitopes of the flagellin protein and tested them for binding to serum from patients with Lyme neuroborreliosis. We also tested those epitopes for binding to a murine monoclonal antibody directed against the B. burgdorferi flagellin protein.

The murine monoclonal antibody Mab H9724 (kindly provided by A. Barbour) is directed against the B. burgdorferi flagellin antigen but also demonstrates binding to neuronal tissue. We first used immunoblot analysis as in Example III and found that Mab H9724 bound to an epitope residing in fragment F of the flagellin antigen of B. burgdorferi. Accordingly, we began by constructing eight plasmids containing overlapping epitopes within Fragment F (amino acids 197-241) of the B. burgdorferi flagellin protein. We designated these fragments F1–F8.

To prepare these fragments, we used oligonucleotide primers corresponding to both strands of fragments defined by nucleotides 586-621 (F1), 598-623 (F2), 613-634 (F3), 625-660 (F4), 637-675 (F5), 649-684 (F6), 667-702 (F7), and 685-729 (F8). As in Example II, supra, the oligonucleotides were flanked by overhanging EcoR1 and BamH1 restriction enzyme sites to facilitate subcloning.

We mixed together individual plus and minus strand oligonucleotides in equimolar amounts (1 mM) in water. We then heated the mixture to 90° C. for 5 minutes and cooled to room temperature overnight. We then cloned the annealed oligonucleotides into pMX and used the recombinant plasmids to transform E. coli DH5α. We then expressed the flagellin epitopes in E. coli as glutathione transferase fusion proteins and purified them as in Example II.

By performing immunoblots with fragments F1 to F8 as in Example III, we localized Mab H9724 binding to F4 and F5, which encompassed amino acids 209–225. The overlapping amino acids in these two fragments included amino acids 213–221. It is likely therefore, that the monoclonal antibody that binds to neuronal tissue recognizes an epitope highly homologous to acids 213–221 of the B. burgdorferi flagellin protein.

To determine the fine specificity of the human serologic response to epitopes within fragment F, we tested 37 patients' sera by immunoblotting using fragments F1–F8. All serum samples were collected from patients that tested positive on a standard ELISA for Lyme disease. The results are summarized in FIG. 4. Patients 8, 9, 13, 18–22 and 31 had erythema migrans. Patients 5, 11 and 14 had neuroborreliosis (encephalitis, peripheral neuritis and weakness respectively).

Figure 4B:
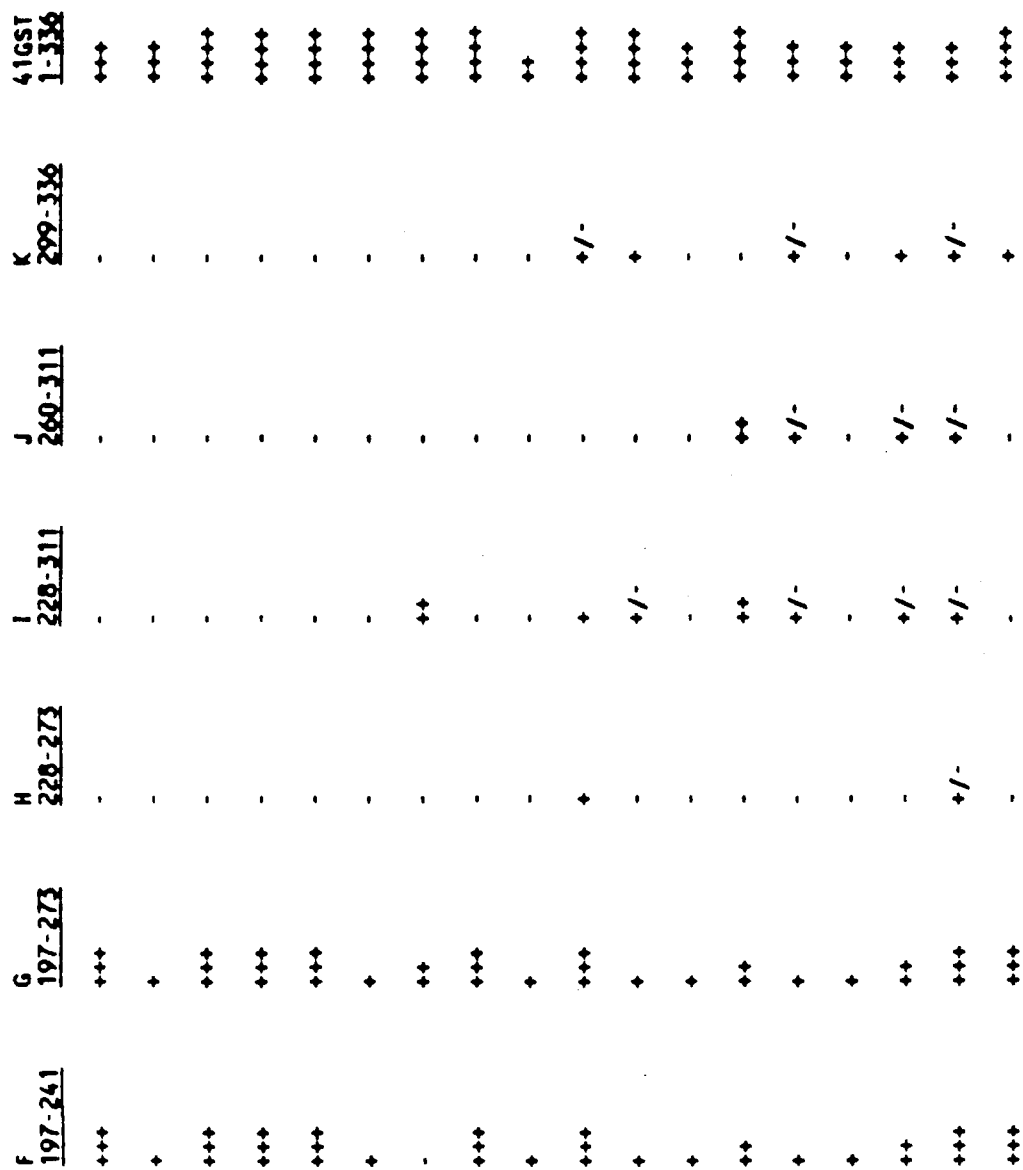

As can be seen from FIG. 4, 35 of 37 patients showed reactivity with fragment F. Of the 35 patients' sera which bound fragment F, 27 sera bound to F4 or F5. Specifically, 22 patients' sera bound to F4 and 19 bound to F5. All three patients with neurologic symptoms bound to F5 and two of those patients' sera bound to F4.

To determine if sera from patients with neurologic Lyme disease and Mab H9724 bound to a neuroblastoma cell line, we performed immunofluorescence studies. The results were in agreement with previous work and indicated that Mab H9724 and sera from patients with neurologic disease bound to neuroblastoma cells.

We next sought to determine if the binding in patients' sera was specific for the epitope residing in fragment F. To do this we incubated patient sera with a peptide corresponding to amino acids 213–224 of the flagellin protein, i.e. the peptide of SEQ ID NO: 1. We then conducted immunofluorescence studies using the adsorbed serum to determine if it retained the ability to bind to a neuroblastoma cell line.

The cell line we used was SH-K-SH, available from ATCC (No. HTB 11). We grew the cells to confluence in RPMI 1640 with 10% fetal calf serum, 300 mg/L L-glutamine and penicillin/streptomycin. To perform the immunofluorescence, we treated coverslips overnight with 0.1N HCl, autoclaved them, and placed them into 35 mm Petri dishes. We then placed two mls of culture medium containing $2 \times 10^5$ cells in each plate. The cells were allowed to attach for 24 hours. We then aspirated the medium, washed the coverslips 3 times with PBS, incubated the coverslips with cells in 3.7% formaldehyde in PBS for 15 minutes, and washed three times with PBS.

To prepare the serum for immunofluorescence, we prepared the 213–224 peptide at 2 mg/ml in PBS. The patient's sera was diluted 1:800. Equal volumes of the peptide and the sera were mixed and incubated for 1 hour at room temperature. We then centrifuged the samples for 10 minutes at 8000 x g and used the supernatant for immunofluorescence.

We incubated the coverslips with the adsorbed sera for 30 minutes at 37° C., washed 3 times, incubated with FITC goat anti-human GAM diluted 1:30 for 30 minutes at 37° C. and again washed 3 times. The coverslip, with a drop of mounting oil, was placed on a slide and examined by fluorescence microscopy.

The results of these studies showed that binding to the neuroblastoma cell line was eliminated by adsorption of the sera with the 213–224 peptide. We also determined that incubation of Mab H9724 with the peptide also eliminated its ability to bind to the neuroblastoma cell line. These data indicate that antibody to the flagellin epitope residing within amino acids 213–224 specifically accounts for cross reactivity between antibodies to flagellin and neuronal tissue.

The peptide of SEQ ID NO: 1 is therefore useful not only as a diagnostic agent. It is also useful in a variety of methods as a therapeutic or prophylactic agent for neuroborreliosis, arthritis, carditis and other symptoms of Lyme disease, due to its cross-reactivity with anti-*B. burgdorferi* antibodies which contribute to Lyme disease by binding to neuronal tissue. For example, the peptide of SEQ ID NO: 1 and other neuroborreliosis-associated antigens may be used to adsorb antibodies in the serum of patients infected with *B. burgdorferi*. After allowing the peptide to bind to the anti-*B. burgdorferi* antibodies in the patient's serum, antigen-antibody complexes could be removed or destroyed.

In this regard, a patient's blood could be cycled through a column containing either the immobilized peptide of SEQ ID NO: 1 or fragments thereof or derivatives thereof, so that the undesirable antibodies present in the blood may be removed.

Similarly, toxic agents which are designed to target specific molecules could be used in conjunction with this peptide to block or remove these antibodies in vivo or in vitro.

We claim:

1. A flagellin polypeptide capable of detecting *B. burgdorferi*-specific antibodies in a majority of seropositive samples and comprising an immunodominant region of a *B. burgdorferi* flagellin antigen or derivatives thereof, which polypeptide is recognized by antibodies elicited by infection with *B. burgdorferi*, but is substantially less reactive than the full-length flagellin protein when reacted with antibodies elicited by infection with other bacteria or treponemes.

2. The flagellin polypeptide according to claim 1, wherein the polypeptide comprises an immunodominant region having amino acids 165–273 of a *B. burgdorferi* flagellin protein (SEQ ID NO: 19) or fragments or derivatives of said region that retain the immunological activity of an immunodominant region.

3. The flagellin polypeptide according to claim 1, wherein the polypeptide comprises an immunodominant region having amino acids 197–273 of a *B. burgdorferi* flagellin protein (SEQ ID NO: 19 a.a. 33–108) or fragments or derivatives of said region that retain the immunological activity of an immunodominant region.

4. The flagellin polypeptide according to claim 1, wherein the polypeptide comprises an immunodominant region having amino acids 197–241 of a *B. burgdorferi* flagellin protein (SEQ ID NO: 19 a.a. 33–76) or fragments or derivatives of said region that retain the immunological activity of an immunodominant region.

5. A fusion protein comprising a flagellin polypeptide according to any one of claims 1–4.

6. A multimeric protein comprising a flagellin polypeptide according to any one of claims 1–4.

7. A diagnostic kit comprising a flagellin polypeptide according to any of claims 1–4 and instruction for using said kit.

8. The flagellin polypeptide according to claim 1, wherein the polypeptide is immunologically reactive with antibodies which are immunologically reactive with antigens associated with neuronal tissue.

9. The flagellin polypeptide according to claim 8, wherein the polypeptide comprises a peptide fragment having the amino acid sequence set forth in SEQ ID NO: 1.

10. A diagnostic kit comprising a flagellin polypeptide according to claim 8 or 9 and instructions for use.

11. The diagnostic kit according to claim 7 or 10, further comprising a *B. burgdorferi* OspA or OspB polypeptide.

* * * * *